US00PP12563P2

(12) United States Plant Patent
Olesen et al.

(10) Patent No.: US PP12,563 P2
(45) Date of Patent: Apr. 23, 2002

(54) SHRUB ROSE PLANT NAMED 'POULRIA'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/274,686

(22) Filed: Mar. 24, 1999

(51) Int. Cl.[7] ..... A01H 5/00

(52) U.S. Cl. ..... Plt./108
(58) Field of Search ..... Plt./108, 129

(56) References Cited

PUBLICATIONS

Copy of NL PBR R002155, filed on Jan. 8, 1994 and NL Grant #15161 published May 30, 1995.*

Copy of PL PBR ROA0220, filed on Aug. 31, 1995 and PL Grant #000738 published on Mar. 31, 1998.*

Copy of EU 0600/95, filed August 8, 1995, and EU 0620 granted August 2, 1996.*

UPOV–ROM, 2000/04, Plant Variety Database, GTI Jouve Retrieval Software, 4 citations for 'POULria'.*

* cited by examiner

*Primary Examiner*—Howard J. Locker

(57) ABSTRACT

A new garden rose plant which has abundant, red flowers, a low spreading habit and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between two unnamed seedlings. The two parents were crossed and the resulting seeds were planted in a controlled environment. The new variety is named 'POULria'.

The new rose may be distinguished from its seed parent, an unnamed seedling by the same inventors, by the following combination of characteristics:

1. The seed parent is a floribunda rose; whereas, 'POULria' is a shrub rose;
2. The seed parent has larger blooms and more petals than 'POULria';
3. The habit of the seed parent is upright, while the habit of 'POULria' is low and spreading.

The new variety may be distinguished from its pollen parent, unnamed seedling created by the same inventors, by the following combination of characteristics:

1. The pollen parent is a miniature rose, much smaller than 'POULria';
2. The pollen parent has orange-red flowers; whereas, 'POULria' has dark-red flowers.

The objective of the hybridization of this rose variety for garden use was to create a new and distinct variety with unique qualities, such as:

1. Uniform and abundant flowers;
2. Vigorous, compact growth;
3. Low growing, spreading habit;
4. Dark-red blooms.

This combination of qualities is not present in previously available commercial cultivars of this type and distinguishes 'POULria' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULria' was selected by the inventors in the spring, 1988 as a single plant from the progeny of the aforementioned hybridization.

Asexual reproduction of 'POULria' by cuttings and traditional budding was first done by L. Pernille and Mogens N. Olesen in August, 1988 in a nursery in Fredensborg, Denmark. This initial and other subsequent propagations conducted in controlled environments have demonstrated that the characteristics of 'POULria' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves and stems of 'POULria'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULria', as observed in its outdoor growth in a field nursery in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULnino', a shrub rose variety from the same inventors described and illustrated in U.S. Plant Pat. No. 9,554 and issued on May 21, 1996 are compared to 'POULria' in Chart 1.

CHART 1

| | 'POULria' | 'POULnino' |
|---|---|---|
| Bloom size when fully open. | 34-38 mm. | 45-55 mm. |
| Petalage. | Very double, 40-50 petals. | Semi-double, 18-22 petals. |
| Bloom color, upper surface; open bloom. | Red Group 53A. | Red Group 46A-46B |

Parents:
- *Seed parent.*—Unnamed seedling.
- *Pollen parent.*—Unnamed seedling.

Classification:
- *Botanical.*—*Rosa hybrida.*
- *Commercial.*—Shrub.

FLOWER AND FLOWER BUD

Blooming habit: Recurrent.

Flower bud:
- *Size.*—Upon opening, 15 mm–20 mm in length from base of receptacle to end of bud.
- *Bud form.*—Short, globular.
- *Bud color.*—As sepals unfold, Red Group 53A. Red Group 53A at ¼ opening.
- *Sepals.*—Yellow-Green Group 146B. Red intonations of Greyed-Red Group 180A on some sepals. Weak foliaceous appendages on three of the five sepals. Surfaces of sepals moderately pubescent. Stipitate glands are present on margins of sepals with appendages.
- *Receptacle.*—Surface: Smooth, some with a small numbers of fine white hairs. Shape: Funnel shaped. Size: Small to Medium, 5 mm (h)×5 mm (w). Color: Yellow-Green Group 146B with intonations of Greyed-Red Group 180A.
- *Peduncle.*—Surface: Smooth, limited numbers of stipitate glands. Length: 35–40 mm average length. Color: Yellow-Green Group 146B–146C with intonation of Greyed-Red Group 180A. Strength: Erect.
- *Pedicel.*—Surface: Smooth. Length: 40 to 50 mm. Color: Greyed-Red Group 180A with intonations of Yellow-Green Group 146B near bract.
- *Borne.*—Multiple buds per stem, with 16–20 buds per flowering stem.

Flower bloom:
- *Fragrance.*—Light floral fragrance.
- *Duration.*—The blooms have a duration on the plant of approximately 4 to 6 days. Petals fall cleanly away from plant.
- *Size.*—Average flower diameter is 34–38 mm when open.
- *Form.*—Sprays of cup shaped flowers. Shape of flower when viewed from the side: Upon opening, upper part: Flattened convex. Upon opening, lower part: Flattened convex. Open flower, upper part: Flat. Open flower, lower part: Flat.
- *Petalage.*—Very double Average range: 40–50 petals under normal conditions with 4–8 petaloids.

Color:
- *Upon opening, petals.*—Upper Surface: Red Group 53A. Reverse Side: Red Group 53A to Red-Purple Group 59C.
- *Upon opening, basal petal spots.*—Outer Side: White Group 155C. Inner Side: White Group 155C.
- *After opening, petals.*—Upper Surface: Red Group 53A. Reverse Side: Red Group 53A to Red-Purple Group 59C.
- *After opening, basal petal spots.*—Outermost petals: Outer Side: White Group 155C. Inner Side: White Group 155C.

General tonality: On open flower Red Group 53A. No change in the general tonality at the end of the 4th day. Afterwards, general tonality is Red Group 46A.

Petals:
- *Petal reflex.*—Petals reflexed.
- *Petal edge.*—Uniform with point in center of margin.
- *Shape.*—Obovate.
- *Petaloids.*—Present. Quantity: 4–8.
- *Thickness.*—Moderate.
- *Arrangement.*—Informal.

Reproductive organs:
- *Pollen.*—Color: Yellow-Orange Group 15C. Quantity: Average.
- *Anthers.*—Size: Medium. Color: Immature: Yellow Group 12C. Mature: Brown Group 200D. Quantity: Average.
- *Filaments.*—Color: Green-Yellow Group 1B.
- *Stigmas.*—Stigmas are superior in location to anthers. Color: Yellow-Green Group 145D.
- *Styles.*—Color: Green-White Group 157A on lower portion of styles. Upper ⅔ of the styles are Red-Purple Group 61A.
- *Hips.*—None observed.

PLANT

Plant growth: Moderate compact, When grown as a budded field grown plant on *Rosa multiflora* understock. the average height of the plant itself is 65 cm and the average width is 65 cm.

Stems:
- *Color.*—Young wood: Yellow-Green Group 144A–144B. Older wood: Yellow-Green Group 144B.
- *Thorns.*—Incidence: 12 to 15 per 10 cm of stem. Size: Average length: 4–5 mm. Color: Greyed-Orange Group 166D. Shape: Slightly Concave.
- *Surface.*—Young wood: Smooth. Older wood: Rough.

Plant foliage: Normal number of leaflets on leaves in middle of the stem: 5 leaflets.
- *Leaf size.*—Small, 60–70 mm (l)×35–40 mm (w).
- *Abundance.*—Average.
- *Color.*—Upper Leaf Surface: Green Group 137B. Lower Leaf Surface: Yellow-Green Group 147C. Juvenile foliage: Upper surface is Yellow-Green Group 147B. Lower surface is Yellow-Green Group 147B.

*Anthocyanin.*—Limited. Location: Lower leaf surfaces, stems, peduncle, petiole, rachis. Color: Greyed-Red Group 180A.

Plant leaves and leaflets:

*Stipules.*—Size: 15 mm–18 mm. Color: Yellow-Green Group 146C. Stipitate glands: Limited numbers on margins of leaves.

*Petiole.*—Length: 18 mm–22 mm. Color: Yellow-Green Group 146C. Underneath: Smooth. Margins: Limited numbers of stipitate glands present.

*Rachis.*—Color: Yellow-Green Group 146C. Underneath: Smooth. Margins: Limited Numbers of stipitate glands present.

*Leaflet.*—Edge: Serrated. Shape: Ovate to elliptic. Texture: Matte finish, thin.

Disease resistance: Average resistance to mildew, black spot, and Botrytis under normal growing conditions in Jackson County, Oreg.

Cold hardiness: 'POULria' has been found to be cold hardy in Fredensborg, Denmark and in Jackson County, Oreg.

We claim:

1. A new and distinct variety of rose plant of the shrub class, substantially as herein illustrated and described as a distinct and novel rose variety due to its abundant, dark-red flowers, vigorous growth, low spreading habit, and extended period of bloom.

* * * * *

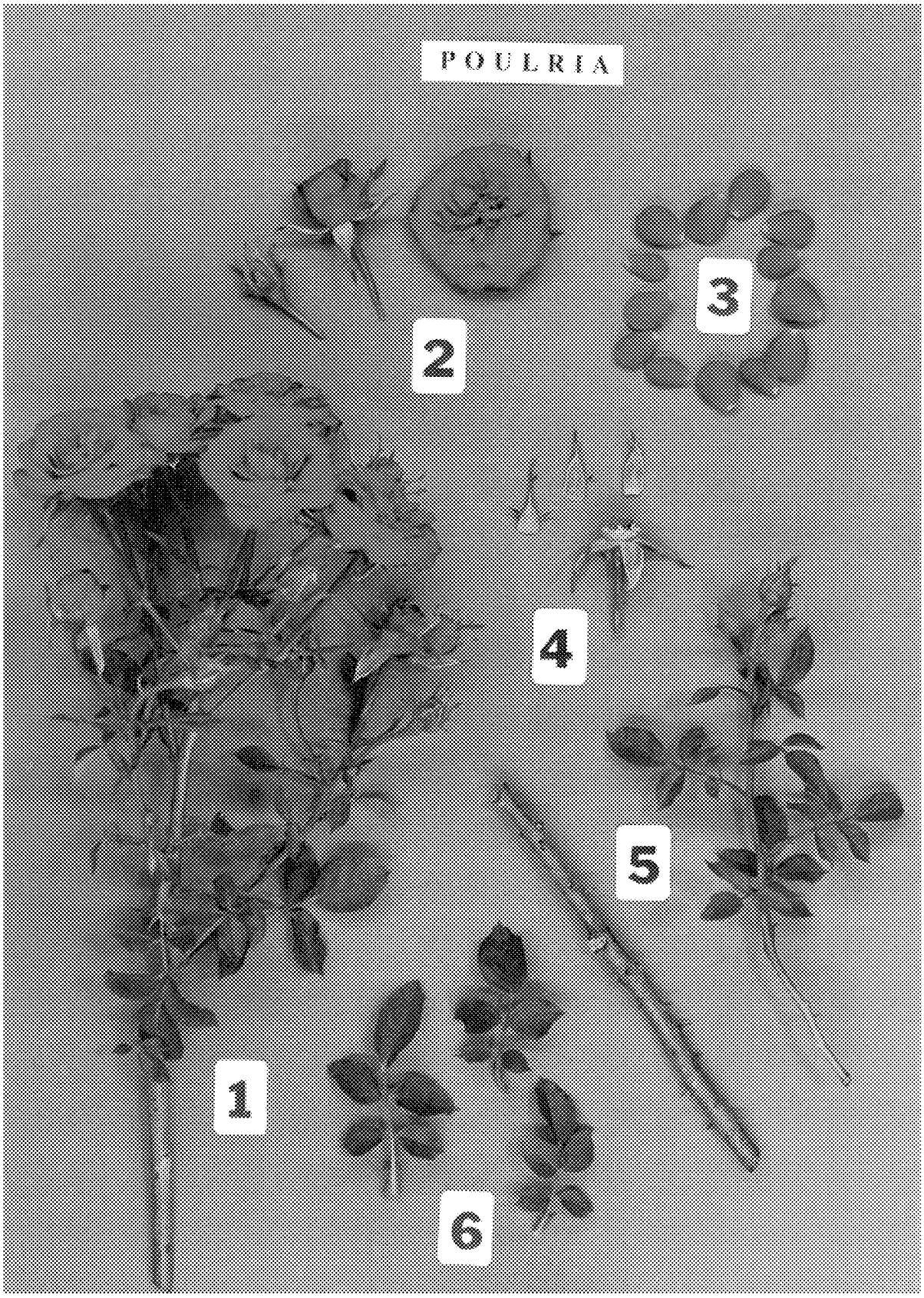
POULRIA
2
3
4
5
1
6